(12) United States Patent
Miller

(10) Patent No.: US 8,062,599 B2
(45) Date of Patent: Nov. 22, 2011

(54) OXYGENATE CONVERSION REACTOR CATALYST COOLERS

(75) Inventor: Lawrence W. Miller, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 149 days.

(21) Appl. No.: 12/571,853

(22) Filed: Oct. 1, 2009

(65) Prior Publication Data

US 2010/0028224 A1    Feb. 4, 2010

Related U.S. Application Data

(62) Division of application No. 11/026,237, filed on Dec. 30, 2004, now abandoned.

(51) Int. Cl.
*F27B 15/08* (2006.01)

(52) U.S. Cl. ......... 422/144; 585/809; 585/822; 422/146

(58) Field of Classification Search .................. 422/140, 422/144, 146; 585/809, 822; 165/104.18
See application file for complete search history.

(56) References Cited

U.S. PATENT DOCUMENTS

| | | | | |
|---|---|---|---|---|
| 4,353,812 A * | 10/1982 | Lomas et al. | .................... | 502/43 |
| 5,324,418 A * | 6/1994 | Muldowney | ............. | 208/120.01 |
| 5,343,929 A * | 9/1994 | Landua et al. | ................. | 164/262 |
| 5,452,757 A * | 9/1995 | Lomas | ..................... | 165/104.16 |
| 5,571,482 A * | 11/1996 | Long et al. | ..................... | 422/144 |
| 7,388,120 B2 * | 6/2008 | van Egmond | ................. | 585/809 |

* cited by examiner

*Primary Examiner* — Nina Bhat
(74) *Attorney, Agent, or Firm* — Arthur E Gooding

(57) ABSTRACT

A catalyst cooled is employed for converting oxygenates to light olefins. The catalyst becomes spent as deposits from the reaction clog up pores on the catalyst surface. A portion of the spent catalyst is regenerated in a regenerator and a portion is circulated back to contact more of the oxygenate feedstream. A catalyst cooler attached to the reactor can cool the spent catalyst circulated through the cooler before the spent catalyst contacts more of the oxygenate feedstream. In an embodiment, all of the spent catalyst that enters the catalyst cooler is withdrawn from the bottom of the catalyst cooler.

5 Claims, 1 Drawing Sheet

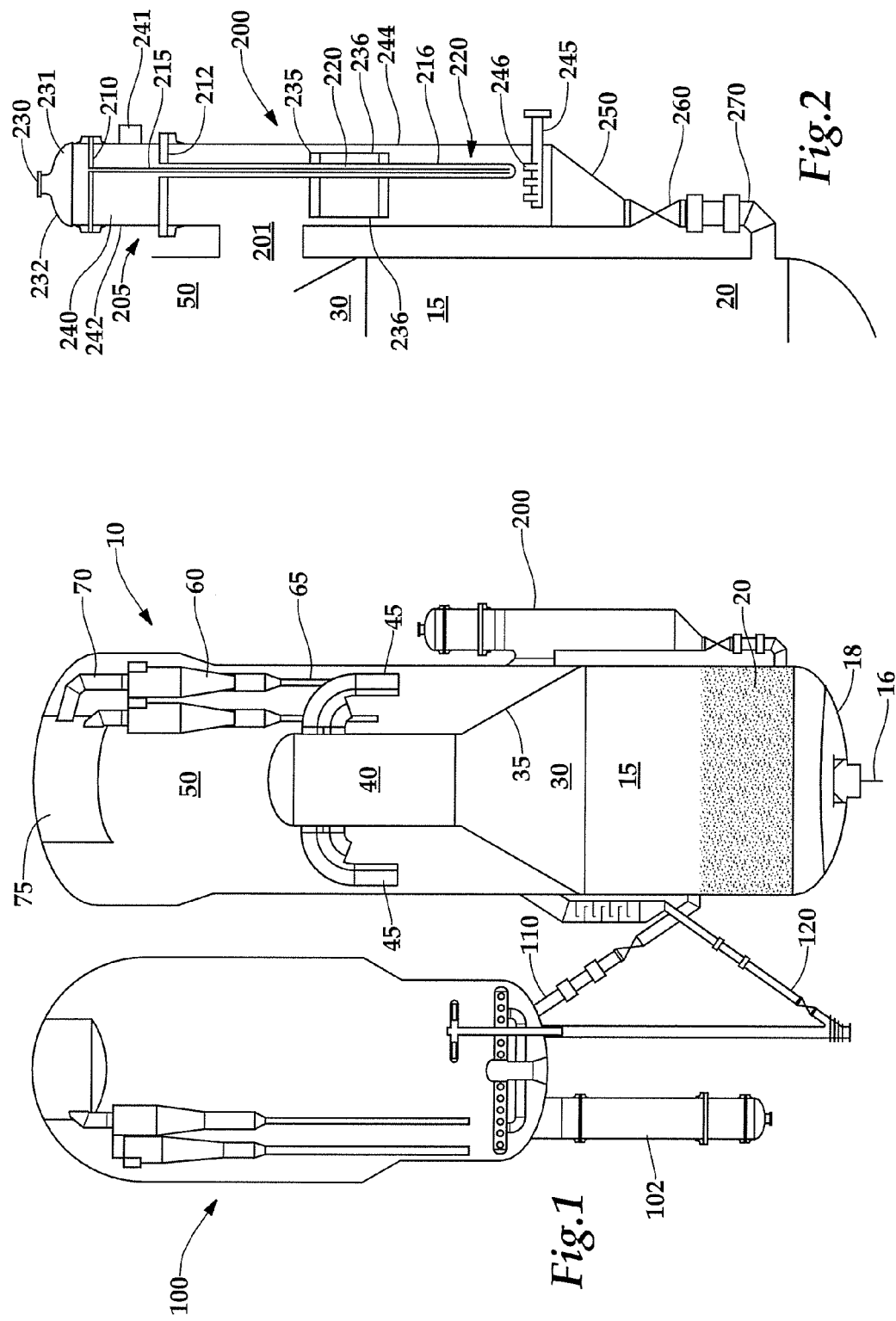

OXYGENATE CONVERSION REACTOR CATALYST COOLERS

CROSS-REFERENCE TO RELATED APPLICATION

This application is a Division of prior application 11/026,237, now abandoned, which was filed Dec. 30, 2004, the contents of which are incorporated herein by reference thereto.

BACKGROUND OF THE INVENTION

This invention relates to a method and apparatus for cooling catalyst in a reactor used in an oxygenate to olefin conversion process.

DESCRIPTION OF THE PRIOR ART

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals.

The search for alternative materials for light olefin production has led to the use of oxygenates such as alcohols and, more particularly, to the use of methanol, ethanol, and higher alcohols or their derivatives. Molecular sieves such as microporous crystalline zeolite and non-zeolitic catalysts, particularly silicoaluminophosphates (SAPO), are known to promote the conversion of oxygenates to hydrocarbon mixtures in a reactor.

When a catalyst is exposed to oxygenates, such as methanol, to promote the reaction to olefins, carbonaceous material (coke) is generated and deposited on the catalyst. Accumulation of coke deposits interferes with the catalyst's ability to promote the reaction and results in a spent catalyst. As the amount of coke deposit increases, the catalyst loses activity and less of the feedstock is converted to the desired olefin product. The step of regeneration removes the coke from the catalyst by combustion with oxygen, restoring the catalytic activity of the catalyst. The regenerated catalyst may then be exposed again to oxygenates to promote the conversion to olefins.

The process of converting oxygenates to light olefins is exothermic. Excess heat from the exothermic reaction can disrupt the conditions necessary for optimal conversion in the reactor by raising the temperature too high. Controlling the temperature within the reactor is needed to optimally convert oxygenates to light olefins and minimize the production of by-products. The reactor temperature can be controlled by steadily removing heat from the reactor during the conversion process. One method of removing heat from the reactor may be accomplished by cooling the catalyst used in the conversion reaction.

Catalyst coolers are typically used for oxygenate conversion regenerators. Without the heat removal from a large catalyst circulation rate, the equilibrium regenerator temperature would be too high. Hence, some external means of heat removal is typically necessary. However, the reactor also heats up during the exothermic reaction of oxygenates to light olefins. The temperature in the reactor also must be controlled.

What is needed is a convenient and efficient way to control the temperature of the reactor in conversions of oxygenates to light olefins.

SUMMARY OF THE INVENTION

This invention provides a process of converting oxygenates to light olefins in which an oxygenate feedstream contacts catalyst and converts to light olefins while spending the catalyst. A first portion of the catalyst is regenerated and a second portion of the catalyst is cooled without being regenerated. Both the regenerated catalyst and the cooled catalyst further contact an oxygenate feedstream. In one aspect, the second portion of the catalyst may be cooled in a catalyst cooler by indirect heat exchange. In a further aspect, a heat exchange fluid is introduced into catalyst cooler near its top and spent catalyst exits near bottom of the catalyst cooler. In one embodiment, a fluidizing medium may be introduced into the catalyst cooler. In an embodiment, another portion of catalyst is returned to contact the oxygenate feedstream without undergoing regeneration or cooling.

In one aspect of the invention, the process includes charging a lower region of a reactor with catalyst, introducing the oxygenates into the lower region and contacting the catalyst, converting the oxygenates into light olefins while spending the catalyst, transporting the light olefins and spent catalyst into an upper region of the reactor, separating the spent catalyst from the light olefins, splitting the spent catalyst into a first portion and a second portion, regenerating the first portion in a regenerator and returning the first portion to the lower reactor region, cooling a second portion in a catalyst cooler having a bottom, withdrawing the second portion from the bottom of the catalyst cooler and returning the second portion to the lower reactor region. In an embodiment, another portion of catalyst is returned to contact the oxygenate feedstream without undergoing regeneration or cooling.

In a further aspect of the invention, a catalyst cooler has a vessel having a bottom and a catalyst inlet, a plurality of cooling tubes located within the vessel, a fluidizing gas distributor located below the cooling tubes, and a catalyst outlet located at the bottom of the vessel. In one aspect, each one of the plurality of cooling tubes includes an inner tube and an outer tube. In a further aspect, the catalyst cooler includes an inlet manifold in fluid communication with the inner tube and an outlet manifold in fluid communication with the outer tubes and the inner tubes fluidly communicating with the outer tubes.

In a still further aspect of the invention, an apparatus for converting oxygenates to light olefins has a reactor for contacting an oxygenate feedstream with catalyst and converting the feedstream to olefin product, a separator for separating spent catalyst from the olefin product, a regenerator for regenerating a first portion of the spent catalyst, a catalyst cooler for cooling a second portion of the spent catalyst and the catalyst cooler including an inlet for heat exchange fluid near the top of the catalyst cooler. In a further aspect, the catalyst cooler includes an inlet manifold for distributing heat exchange fluid, the inlet manifold in fluid communication with inner tubes and an outlet manifold in fluid communication with outer tubes and the inner tubes fluidly communicating with the outer tubes. In a further aspect, the inlet manifold is located near a top of the catalyst cooler. In a further aspect, the catalyst cooler includes a catalyst outlet at the bottom of the catalyst cooler. In a further aspect, the catalyst cooler includes a catalyst inlet above the catalyst outlet. In a further aspect, a distributor for distributing fluidizing medium is located below the outer tubes. In a further aspect, the inlet tubes are suspended from above the catalyst inlet.

BRIEF DESCRIPTION OF THE DRAWINGS

FIG. 1 is a side view of a methanol to olefin reaction reactor and regenerator.

FIG. 2 is an enlarged view of a methanol to olefin reactor catalyst cooler as seen in FIG. 1.

DETAILED DESCRIPTION OF THE INVENTION

Light oxygenates comprising methanol, ethanol, dimethylether, diethylether, or mixtures thereof, may be changed to light olefins such as ethylene or propylene in the presence of silicoaluminophosphate (SAPO) catalyst in an exothermic reaction. Methanol and dimethylether are particularly preferred oxygenate feed stocks. The light oxygenates are introduced to the catalyst via a fluidized feedstream, which is preferably vaporized but may be liquid. The product or products obtained from the conversion process will depend on the feedstream, catalyst and conditions employed. Preferably products are hydrocarbons in the $C_2$ to $C_6$ carbon range. In one aspect, the desired product preferably contains light olefins having from about 2 to 4, more preferably from about 2 to 3 carbon atoms per molecule. The methanol to olefin conversion process may be a vapor phase, fluid catalytic process that converts methanol to olefins, primarily ethylene and propylene.

A generally non-reactive diluent in the feedstream may be used to maintain the selectivity of the catalyst to produce light olefins, particularly ethylene and propylene. Examples of diluents which may be used are helium, argon, nitrogen, carbon monoxide, carbon dioxide, hydrogen, steam, paraffinic hydrocarbons (e.g., methane), aromatic hydrocarbons (e.g., benzene, toluene), and mixtures thereof. The amount of diluent used can vary considerably and is usually from about 5 to about 90 mol-% of the feedstock and preferably from about 25 to about 75 mol-% of the feedstock. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons.

A methanol to olefin unit designed to process about 2,500,000 metric tons per year of 95 wt-% methanol may have a feed rate of preferably between about 1500 and about 4000 kMTA and more preferably between about 2000 and about 3500 kMTA. The feedstream may comprise between about 0 and about 35 wt-% and more preferably between about 5 and about 30 wt-% water. The methanol in the feed stream may comprise between about 70 and about 100 wt-% and more preferably between about 75 and about 95 wt-% of the feedstream. The ethanol in the feedstream may comprise between about 0.01 and about 0.5 wt-% and more typically between about 0.1 and about 0.2 wt-% of the feedstream although higher concentrations may be beneficial. When methanol is the primary component in the feedstream, the higher alcohols in the feedstream may comprise between about 200 and about 2000 ppmw and more typically between about 500 and about 1500 ppmw. Additionally, when methanol is the primary component in the feedstream, dimethyl ether in the feedstream may comprise between about 10 and about 60 ppmw and more typically between about 20 and about 50 ppmw.

During the conversion of oxygenates to light olefins, a carbonaceous material, i.e., coke, is deposited on the catalyst. The coke deposit material has the effect of reducing the number of active sites on the catalyst which thereby affects the extent of the conversion. Thus, during the fluidized bed conversion process, a portion of the coked catalyst is withdrawn from the reactor and regenerated in a regenerator to remove at least a portion of the coke. Preferably, the coke is removed from the catalyst by oxidative regeneration in regenerator. After the catalyst is regenerated to remove coke deposit material, and thereby increase the amount of active catalyst sites, the regenerated catalyst returns to the reactor and further contacts the feedstream in order to convert oxygenates to light olefins. The rate of addition is selected so that a sufficient quantity of active catalyst sites are provided within the fluidized reaction chamber in order to enhance the conversion of the feedstream to the desired product without enhancing the conversion to undesired by-products.

Reaction conditions for the conversion of oxygenates to light olefins are known to those skilled in the art. Preferably, in accordance with the present invention, reaction conditions comprise a temperature between about 200° and about 700° C., more preferably between about 300° and 600° C., and most preferably between about 400° and about 550° C. The reactions conditions are variable depending on the desired products. If more ethylene is desired, then the reactor temperature is preferably between about 475° and about 550° C. and more preferably between about 5000 and about 520° C. If more propylene is desired, then the reactor temperature is preferably between about 350° and about 475° C. and more preferably between about 400° and about 430° C. The light olefins produced can have a ratio of ethylene to propylene of between about 0.5 and about 2.0 and preferably between about 0.75 and about 1.25. If a higher ratio of ethylene to propylene is desired, then the reaction temperature is higher than if a lower ratio of ethylene to propylene is desired.

The temperature of the oxygenate-containing feedstream can be raised and lowered to adjust to the heat from the exothermic reaction of the conversion of oxygenates to light olefins. However, adjusting the temperature of the oxygenate feedstream does not quickly change the temperature of the reaction. The catalyst within reactor is very massive and voluminous. The catalyst is not responsive to changes in the temperature of the feedstream. Moreover, if the catalyst cannot be directly cooled, the reaction can overheat because the reaction is exothermic. If the reaction overheats, apparatus parts of the reaction system can be damaged.

As depicted in FIG. 1, the present invention employs a fast-fluidized bed reactor vessel 10 which comprises an upper disengaging chamber 50 and a lower reaction chamber 15. Lower reaction chamber 15 comprises a dense phase zone 20. Dense phase zone 20 operates within a superficial velocity range at typically between about 0.5 and about 1.5 meters per second. Superficial velocity is the velocity of the gas as it flows through the vessel, determined by dividing the volumetric flow rate of the gas by the cross-sectional area of the vessel. Transition phase zone 30 is disposed above dense phase zone 20 and extends from lower reaction chamber 15 into the upper disengaging chamber 50. Transition phase zone 30 includes a reducing means 35 which reduces the flow path diameter from the diameter of the dense phase zone 20 to the diameter of the riser 40. The superficial velocity within the transition zone preferably is preferably between about 0.5 and about 3 meters per second and more preferably between about 1 and about 2 meters per second.

Feedstock mixed with diluent at effective conditions is introduced into the lower reaction chamber 15 via line 16 and distributor 18 wherein the feedstock is contacted with a partially coked catalyst to selectively produce light olefins. The reaction continues to preferably at least about 80 mol-%, more preferably at least about 85 mol-%, and most preferably at least about 90 mol-% conversion of the oxygenate feedstock with respect to conversion to $C_2$ and $C_3$ olefins. The total conversion to product preferably at least about 90 mol-%, more preferably at least about 95 mol-%, and most preferably at least about 99 mol-% conversion of the oxygenate feedstock.

As the unreacted feedstock and reaction products pass through the dense phase zone 20, they carry partially coked catalyst particles having a reduced number of active catalyst sites into the transition zone 30. The gaseous reaction products and unreacted feedstock lift the spent catalyst to the transition zone 30 at the bottom of a riser 40 section and into the disengaging chamber 50. As the reaction product and the catalyst mixture move upwardly through the lower reaction chamber into a riser section 40, the cross-sectional area of the flow path through the fast-fluidized bed reactor 10 is reduced from the cross-sectional area of the dense phase zone 20 by a cone section 35 to the cross-sectional area of the riser section 40. Riser section 40 discharges the reaction product stream and catalyst mixture through a separation zone consisting of distributor arms 45. Distributor arms 45 discharge the reaction product stream and catalyst mixture to the bottom of disengaging chamber 50. The disengaged catalyst mixture falls to the bottom of disengaging chamber 50 by gravitational force. The pressure in upper disengaging chamber is about 50 kPa (gauge) to about 350 kPa (gauge) and preferably between about 50 kPa gauge and about 300 kPa (gauge), which is about 1–10 kPa lower than in the lower reaction chamber 15. The catalyst that remains in the reaction product stream continues upwardly to phase separators such as cyclones. Cyclones 60 separate catalyst from product vapors. Product vapors are conveyed via conduits 70 to plenum chamber 75 and then to product recovery. Catalyst separated in cyclones 60 drop through dip legs 65 into the bottom of disengaging chamber 50. Valves at the bottom of cyclones 60 prevent backflow of catalyst up dip legs 65. A portion of the spent catalyst settling into bottom of disengaging chamber 50 is directed into a catalyst cooler 200. Another portion of the spent catalyst in the bottom of the disengaging chamber 50 is directed into regenerator 100 through conduit 120. In the regenerator 100, coke deposits are combusted from the catalyst by contact with oxygen-containing gas. Regenerated catalyst particles may be cooled by a back-mix type cooler 102 located at the bottom of regenerator 100. The regenerated catalyst particles are returned to reactor 10 through conduit 110. Another portion of the spent catalyst which represents the majority of spent catalyst in the bottom of the disengaging chamber 50 may be recirculated to the lower reaction chamber 15 through recycle conduits which are not shown.

As shown in FIG. 2, at least one catalyst cooler 200 is provided to cool the catalyst transferred from upper disengaging chamber 50 to lower dense phase zone 20. At least two catalyst coolers may be preferred. Catalyst cooler 200 shown in FIG. 2 is a flow-through type cooler. Catalyst cooler 200 can vary in size depending on the amount of product desired. Preferably the diameter of catalyst cooler is between about 1.8 m and about 2.5 m. Catalyst cooling tubes 220 are located in catalyst cooler 200 and cool the catalyst before it returns to dense phase zone 20. Recirculation slide valve 260 controls the amount of catalyst being transferred to dense phase zone 20. The use of cooling tubes 220 allows the recovery and removal of excess heat from the catalyst caused by the exothermic reactions from the conversion of oxygenates to light olefins. Preferably there are between about 50 and about 250 cooling tubes 220 located in catalyst cooler 200 and more preferably between about 75 and 200 cooling tubes 220. Heat is typically removed from the catalyst to produce steam which can be used elsewhere in the complex. Catalyst recirculation valve 260 controls the amount of catalyst exiting and thus entering the catalyst cooler 200 from the reactor 10 and thereby controls the temperature in reactor 10.

Catalyst is withdrawn from disengaging chamber 50 and enters catalyst cooler 200 through catalyst inlet 201 located at the bottom of the disengaging chamber 50 and underneath an upper cooler portion 205 containing inlet nozzles 230 and 241. Catalyst enters catalyst cooler 200 wherein catalyst contacts catalyst cooling tubes 220 containing boiler feed water acting as heat exchange fluid. Catalyst drifts downwardly through catalyst cooler 200 into funnel 250 which directs catalyst through recirculation slide valve 260 into conduit 270 for return to dense phase zone 20. Catalyst travels downwardly through catalyst cooler 200 as soon as it enters through inlet 201. There are no stagnant zones between inlet 201 and conduit 270 in which catalyst can settle. All catalyst that enters catalyst cooler is returned to dense phase zone 20 of the lower reactor chamber 15 of reactor 10.

Catalyst cooler 200 may be "hot-walled" to match reactor 10. The term "hot-walled" means that the metal shells of reactor 10 and cooler 200 are of the same metallurgy without an inner insulative refractory lining. However, in an embodiment, one or both of the shells may be lined with an insulative refractory which is considered "cold-walled." Additionally, parts of the reactor 10 and cooler 200 are preferably lined with an abrasion resistant coating. The shells of the cooler 200 and the reactor 10 may be made of stainless steel.

In an embodiment, boiler feed is water, but other types of heat exchange fluid are contemplated including water with additives to affect the boiling point of the fluid. Boiler feed water enters inlet manifold 231 through cooling medium nozzle 230 at or near the top of catalyst cooler 200. In an embodiment, inlet manifold 231 is defined between an upper head 232 of cooler 200 and an upper tube sheet 210. Preferably catalyst cooling tubes 220 have an inlet and an outlet at or near the top of cooler 200. Preferably catalyst cooling tubes 220 are bayonet-style tubes which each comprise an inner tube 215 and an outer tube 220. Inner tubes 215 of catalyst cooling tubes 220 are secured to and suspended from an upper tubesheet 210. Inlets of inner tubes 215 fluidly communicate with inlet manifold 231. Boiler feed water entering inlet manifold 231 is directed down inner tube 215 of cooling tubes 220. Boiler feed water travels down length of inner tube 215 and exits outlets of inner tubes 215. The boiler feed water then reverses direction and flows up outer tube 216 which surrounds inner tube 215. The catalyst contacts an outer surface of outer tubes 216 of catalyst cooling tubes 220. The diameter of inner tubes 215 is preferably between about 1.9 and about 5.1 cm and more preferably between about 2.5 and about 4 cm. The diameter of outer tubes 216 is preferably between about 3.8 and about 8.9 cm and more preferably between about 5 and about 7 cm.

Heat from the catalyst is indirectly exchanged with boiler feed water in outer tubes 216. The indirect heat exchange raises the temperature of the boiler feed water in outer tubes 216 and converts at least a portion of it to steam. This contact with outer tubes 216 lowers the temperature of the catalyst being transported to lower dense phase zone 20. The heated boiler feed water and steam from outer tubes 216 are directed out of outlets of outer tubes 216 and into outlet manifold 240 defined between upper tube sheet 210, a lower tube sheet 212 and a cylindrical upper shell 242. Outer tubes 216 are secured to and suspend from lower tube sheet 212. Outlets of outer tubes 216 fluidly communicate with outlet manifold 240. Fluid in outlet manifold 240 is then transported out of catalyst cooler 200 through nozzle 240 into a circulation drum where the vapor and heated boiler feed liquid are separated. The cooled catalyst then travels down catalyst cooler 200 and back to reactor 10 through conduit 270.

A fluidizing gas is also directed upwardly in catalyst cooler 200 by distributor 245 with nozzles 246. Preferably distributor 245 is located beneath cooling tubes 220 with nozzles 246 directing the fluidizing gas upwardly in catalyst cooler 200. An inert gas such as nitrogen, steam, or a hydrocarbon gas is used to fluidize the catalyst particles entering catalyst cooler 200 through catalyst inlet 201. Steam may be preferred because it would condense out of the product gases. The flow rate of the fluidizing gas is sufficiently high to accomplish fluidization of the catalyst. The fluidizing gas used in catalyst cooler 200 improves the heat transfer between catalyst and cooling tubes 220 by generating turbulence which enhances the heat transfer coefficient between the catalyst and the cooling tubes 220. The two ways to control the temperature of the circulated catalyst is to either control the amount of catalyst flowing through catalyst cooler 200 by catalyst recirculation valve 260 or to vary the fluidizing gas in catalyst cooler 200.

Upper cooler portion 205, which comprises inlet manifold 231 and outlet manifold 240, is located near the top of catalyst cooler 200. Locating the manifolds 231 and 240 near the bottom of catalyst cooler 200 may foster catalyst settling on parts of a tube sheet. No catalyst will settle on a tube sheet in catalyst cooler 200 because the bottom of the catalyst cooler is defined by funnel 250. Gravitational force pulls catalyst particles downward through catalyst cooler 200, and funnel 250 will facilitate keeping all of the catalyst moving downwardly out of cooler 200. No stagnant area in cooler 200 is provided where catalyst and feed can remain without being returned to reactor 10 for an undesirably long period of time. Upper tube sheet 210 is bolted between a flange at the lower end of head 231 of cooler 200 and an upper flange at an upper end of the upper cylindrical shell 242. Lower tube sheet 212 is welded to the lower end of cylindrical shell 242 and bolted to a flange at an upper end of a lower shell 244 that defines the lower portion of cooler 200. The lower tube sheet preferably has a layer of insulative refractory adhered to the lower surface thereof to keep the upper cooler portion 205 cooler than the rest of the catalyst cooler 200. Grates 235 extend horizontally in the catalyst cooler 200 to stiffen the bundle of cooling tubes 220 vertically aligned in catalyst cooler 200. Grates 235 define openings through which cooling tubes extend. Preferably there are at least two layers of grates 235 in each catalyst cooler 200. Grates are secured to the cooling tubes 220 and to each other by strengthening rods 236 which may be made of the same material as the cooling tubes 220. The grates 235 and the cooling tubes 220 are enabled to thermally expand together as necessary without binding.

The cooling tubes may be made of a chromium-molybdenum-iron alloy because it is resistant to corrosion from trace chlorides in the boiler feed water if used as the heat exchange liquid. However, this alloy is very susceptible to corrosion from acetic acid. Stagnant zones in catalyst cooler 200 may allow cold spots to develop either in normal operation or at shutdown. Unreacted methanol feed can break down to form acetic acid. In cold spots, acetic acid in the vapors can condense out and corrode components in the cooler 200, such as the cooling tubes 220 which are susceptible to corrosion from acetic acid. With inlet manifold 231 and outlet manifold 241 located in upper cooler portion 205 located near the top of catalyst cooler 200, stagnant zones are eliminated in catalyst cooler 200. The present invention avoids stagnant zones by assuring vapors remaining on or with the catalyst travels down or out of the catalyst cooler 200 to return to reactor 10 in a timely fashion. Therefore, accumulation of acetic acid deposits is much less likely.

The benefits of the present invention are that process economics are improved by steam generation. The production of usually high pressure steam can be increased by the heat removal from the catalyst transported through catalyst coolers 200. Second, process control is improved because cooling catalyst will provide much more responsive control of the temperature, as opposed to merely controlling the temperature of the feedstock introduced via line 16 into reactor 10. There are also safety implications in more responsive temperature control of the catalyst because the reaction is exothermic and reactor 10 can overheat, leading to apparatus damage. Third, cooling the catalyst adds process flexibility. In response to process changes such as desired conversion levels heat removal from catalyst coolers can be varied over a much wider range than the standard heat removal technique of internal cooling tubes within reactor 10.

There are two possible embodiments of reactor catalyst coolers to use on reactor 10, a flow-through cooler and a back-mix cooler. For a flow-through cooler, catalyst cooler 200 is situated on the side of reactor 10, as indicated in FIG. 2. Catalyst is directed into catalyst coolers 200 through catalyst inlet 201 and the catalyst flows down catalyst cooler 200 by gravitational force. For a back-mix type cooler, catalyst cooler 200 would be vertically located at the bottom of reactor 10 near distributor 18 at the bottom of dense phase zone 20. The catalyst is fluidized in dense phase 20 so the catalyst will enter and leave the back-mix catalyst cooler due to natural circulation of fluidized particles. The fluidized catalyst particles will fall into a back-mix cooler at the bottom of reactor 10 due to fluidization and gravitational forces. The catalyst will contact cooling tubes 220 in a back-mix cooler and then the fluidizing gas within catalyst cooler 200 will direct the catalyst particles back into the lower reactor chamber 15 of reactor 10. Back-mix type coolers are not as efficient as flow-through type coolers because the catalyst does not contact cooling tubes 220 as much. Some catalyst particles can drift into the back-mix type cooler and then drift back out into reactor 10 without contacting cooling tubes 220 for the entire length of the back-mix cooler. A flow-through cooler is much more effective at removing heat because the catalyst particles entering the flow-through cooler can contact cooling tubes for the entire length of the cooling tubes.

This invention is directed to a process of converting oxygenates to light olefins including contacting an oxygenate feedstream with catalyst and converting the oxygenate feedstream to light olefins while spending the catalyst, regenerating a first portion of the spent catalyst and returning the first portion to contact the oxygenate feedstream, and cooling a second portion of the spent catalyst and returning the second portion to contact the oxygenate feedstream. In a further aspect, the second aspect is cooled in a catalyst cooler by indirect heat exchange. In a further aspect, a heat exchange fluid is introduced into the catalyst cooler from near a top of the catalyst cooler. In a further aspect, spent catalyst exits the catalyst cooler from near the bottom of the catalyst cooler. In yet a further aspect, a fluidizing medium is introduced into the catalyst cooler.

This invention is also directed to a process of converting oxygenates to light olefins including charging a lower region of a reactor with catalyst, introducing the oxygenates into the lower region and contacting the catalyst, converting the oxygenates into the light olefins while spending the catalyst, transporting the light olefins and a portion of spent catalyst into an upper region of the reactor, separating the spent catalyst from the light olefins in the upper region, splitting the spent catalyst into a first portion and a second portion, regenerating the first portion in a regenerator and returning the first portion to the lower region, cooling a second portion in a catalyst cooler having a bottom, withdrawing the second portion from the bottom and returning the second portion to the lower region. In a further aspect, the second portion is cooled in a catalyst cooler by indirect heat exchange. In yet a further aspect, a heat exchange fluid is introduced into the catalyst cooler from near a top of the catalyst cooler and spent catalyst exits the catalyst cooler from near the bottom of the catalyst cooler.

This invention is directed to a catalyst cooler having a vessel having a bottom and a catalyst inlet, a plurality of cooling tubes located within the vessel, a fluidizing gas distributor located below the cooling tubes, and a catalyst outlet located at the bottom of the vessel. In a further aspect, each one of the cooling tubes has an inner tube and an outer tube. In a further aspect, the catalyst cooler has an inlet manifold in fluid communication with the inner tubes and an outlet manifold in fluid communication with the outer tubes and the inner tubes fluidly communicating with the outer tubes. In a further aspect, the inlet manifold is located near a top of the catalyst cooler. In a further aspect, a catalyst outlet is at the bottom of the catalyst cooler and a catalyst inlet above the catalyst outlet.

This invention is directed to an apparatus for converting oxygenates to light olefins having a reactor for contacting an oxygenate feedstream with catalyst and converting the feedstream to olefin product, a separator for separating spent catalyst from the olefin product, a regenerator for regenerating a first portion of the spent catalyst, a catalyst cooler for cooling a second portion of the spent catalyst and the catalyst cooler including an inlet for heat exchange fluid near the top of the catalyst cooler. In a further aspect, the catalyst cooler includes an inlet manifold for distributing heat exchange fluid, the inlet manifold in fluid communication with inner tubes and an outlet manifold in fluid communication with outer tubes and the inner tubes fluidly communicating with the outer tubes. In a further aspect, the inlet manifold is located near a top of the catalyst cooler. In a further aspect, the catalyst cooler includes a catalyst outlet at the bottom of the catalyst cooler. In a further aspect, the catalyst cooler includes a catalyst inlet above the catalyst outlet. In a further aspect, a distributor for distributing fluidizing medium is located below the outer tubes. In a further aspect, the inlet tubes are suspended from above the catalyst inlet.

The invention claimed is:

1. An apparatus for converting oxygenates to light olefins comprising:
   a reactor for contacting an oxygenate feed stream with catalyst and converting said feed stream to olefin product;
   a separator for separating spent catalyst from said olefin product;
   a regenerator for regenerating a first portion of said spent catalyst; and
   a catalyst cooler for cooling a second portion of said spent catalyst, said catalyst cooler including an inlet for heat exchange fluid near the top of said catalyst cooler, wherein the catalyst cooler comprises bayonet-style heat exchange tubes, such that the cooling fluid enters and exits the top of the heat exchanger and the heat exchange fluid does not contact the catalyst.

2. The apparatus of claim 1 wherein said cooler includes an inlet manifold for distributing heat exchange fluid, said inlet manifold in fluid communication with inner tubes and an outlet manifold in fluid communication with outer tubes and said inner tubes fluidly communicating with said outer tubes.

3. The apparatus of claim 1 wherein said inlet manifold is located near a top of said catalyst cooler.

4. The apparatus of claim 1 further including a distributor for distributing fluidizing medium located below said outer tubes.

5. The apparatus of claim 1 wherein said inlet tubes are suspended from above said catalyst inlet.

* * * * *